United States Patent [19]

Scanlon

[11] Patent Number: 5,435,438
[45] Date of Patent: Jul. 25, 1995

[54] RETAINER PACKAGE FOR MULTIPLE SUTURE

[75] Inventor: Christopher Scanlon, Milford, Conn.

[73] Assignee: United States Surgical Corporation, Norwalk, Conn.

[21] Appl. No.: 101,132

[22] Filed: Aug. 2, 1993

[51] Int. Cl.⁶ ............................................. A61B 17/06
[52] U.S. Cl. .................. 206/63.3; 206/227; 206/380
[58] Field of Search ............ 206/63.3, 227, 380, 206/381, 382

[56] References Cited

U.S. PATENT DOCUMENTS

| | | |
|---|---|---|
| D. 263,505 | 3/1979 | Black . |
| D. 272,600 | 2/1981 | Kubas . |
| 2,692,676 | 10/1954 | Grover . |
| 3,136,418 | 6/1964 | Stacy et al. . |
| 3,162,307 | 12/1964 | Regan, Jr. . |
| 3,206,018 | 9/1965 | Lewis et al. . |
| 3,280,971 | 10/1966 | Regan, Jr. . |
| 3,338,401 | 8/1967 | Regan, Jr. . |
| 3,357,550 | 12/1967 | Holmes et al. . |
| 3,363,751 | 1/1968 | Shave et al. . |
| 3,444,994 | 5/1969 | Kaepernik et al. . |
| 3,487,917 | 1/1970 | Shave et al. . |
| 3,545,608 | 12/1970 | Berger et al. . |
| 3,627,120 | 12/1971 | Bordeau . |
| 3,651,935 | 3/1972 | Nysten . |
| 3,759,376 | 9/1973 | Lisowski . |
| 3,779,375 | 12/1973 | Foster . |
| 3,857,484 | 12/1974 | Thyen . |
| 3,869,044 | 3/1975 | Olsson et al. . |
| 3,876,068 | 4/1975 | Sonnino . |
| 3,939,969 | 2/1976 | Miller . |
| 3,972,418 | 8/1976 | Schuler et al. . |
| 3,985,227 | 10/1976 | Thyen et al. . |
| 4,014,434 | 3/1977 | Thyen . |
| 4,034,850 | 7/1977 | Mandel et al. . |
| 4,063,638 | 12/1977 | Marwood . |
| 4,069,912 | 1/1978 | Black et al. . |
| 4,120,395 | 10/1978 | Mandel et al. . |
| 4,126,221 | 11/1978 | Cerwin . |
| 4,135,623 | 1/1979 | Thyen . |
| 4,142,628 | 3/1979 | Marocco et al. . |
| 4,183,431 | 1/1980 | Schmidt et al. . |
| 4,249,656 | 2/1981 | Cerwin et al. . |
| 4,253,563 | 3/1981 | Komarnycky . |
| 4,284,194 | 8/1981 | Flatau . |
| 4,369,880 | 1/1983 | Giggy et al. . |
| 4,391,365 | 7/1983 | Batchelor . |
| 4,406,363 | 9/1983 | Aday . |
| 4,412,613 | 11/1983 | Kubas . |
| 4,412,614 | 11/1983 | Ivanov et al. . |
| 4,413,727 | 11/1983 | Cerwin et al. . |
| 4,424,898 | 1/1984 | Thyen et al. . |
| 4,427,109 | 1/1984 | Roshdy . |
| 4,483,437 | 11/1984 | Cerwin et al. . |
| 4,496,045 | 1/1985 | Ferguson et al. . |
| 4,549,649 | 10/1985 | Roshdy . |
| 4,555,016 | 11/1985 | Aday et al. . |

(List continued on next page.)

FOREIGN PATENT DOCUMENTS

| | | |
|---|---|---|
| 285712 | 9/1966 | Australia . |
| 662417 | 4/1963 | Canada . |
| 698656 | 4/1964 | Canada . |
| 2331638 | 7/1977 | France . |
| 6504467 | 10/1966 | Netherlands . |
| 7302081 | 8/1973 | Netherlands . |
| 680089 | 10/1952 | United Kingdom . |
| 2148232 | 5/1985 | United Kingdom . |
| 2161130 | 1/1986 | United Kingdom . |

*Primary Examiner*—David T. Fidei

[57] ABSTRACT

A suture package for storing a plurality of sutures is disclosed. The package includes a plurality of panel members foldably connected to each other and arranged to fold onto each other to form a plurality of suture compartments for storing an individual suture therein. The package also includes an enclosure card defining at least two card portions. One of the card portions of the enclosure card includes a plurality of tabs and apertures for securing the needled ends of the sutures. The card portions are adapted to fold onto each other to define a compartment to accommodate the folded suture panel members.

34 Claims, 7 Drawing Sheets

U.S. PATENT DOCUMENTS

| | | |
|---|---|---|
| 4,572,363 | 2/1986 | Alpern . |
| 4,574,948 | 3/1986 | Huck et al. . |
| 4,574,957 | 3/1986 | Stead . |
| 4,615,435 | 10/1986 | Alpern et al. . |
| 4,699,271 | 10/1987 | Lincoln . |
| 4,700,833 | 10/1987 | Smith . |
| 4,708,241 | 11/1987 | Black . |
| 4,813,537 | 3/1989 | Okuhara et al. . |
| 4,884,681 | 12/1989 | Roshdy et al. . |
| 4,896,767 | 1/1990 | Pinheiro . |
| 4,946,043 | 8/1990 | Roshdy et al. . |
| 5,048,678 | 9/1991 | Chambers . |
| 5,277,299 | 1/1994 | Holzwarth et al. ................ 206/63.3 |

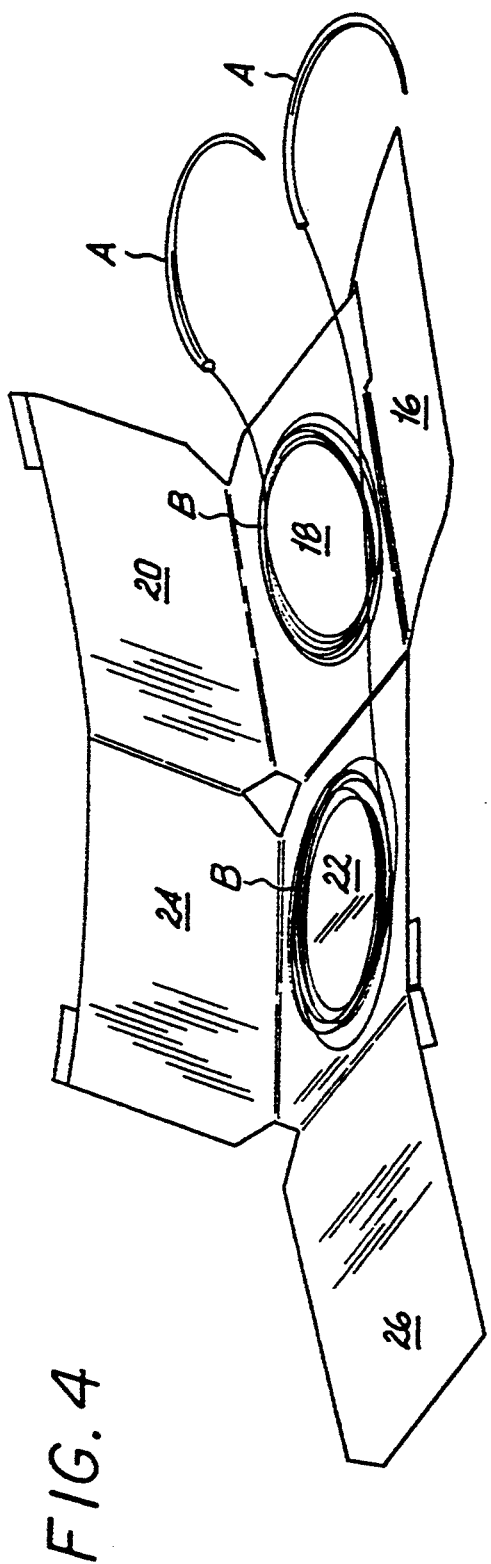
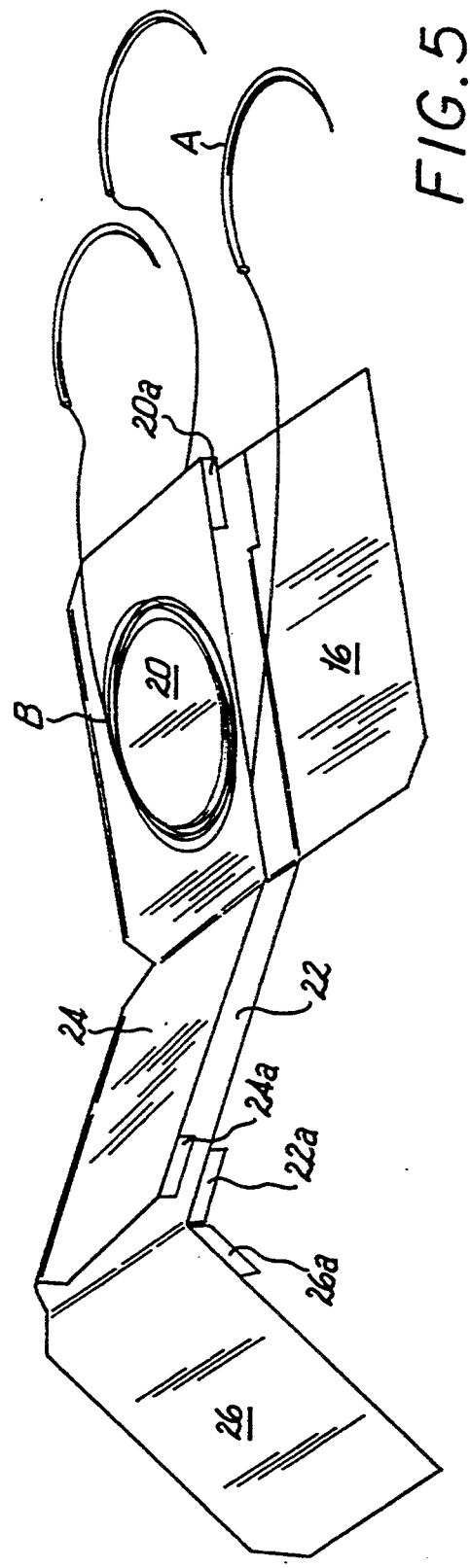
FIG. 4
FIG. 5

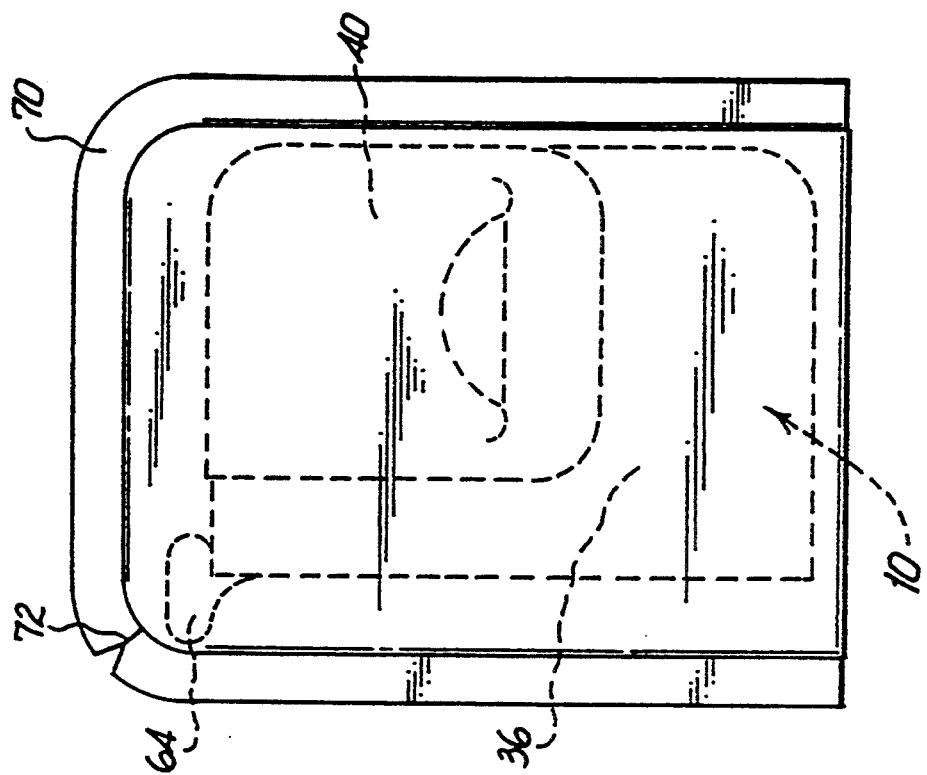
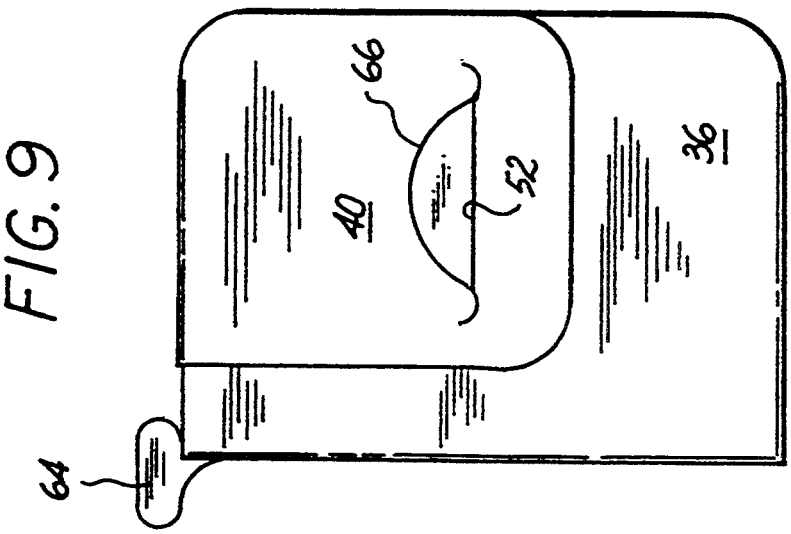
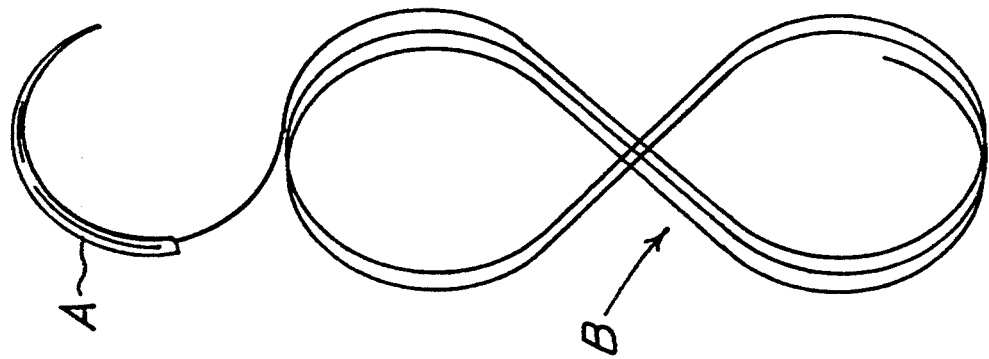

RETAINER PACKAGE FOR MULTIPLE SUTURE

BACKGROUND OF THE INVENTION

1. Field of the Invention

The present invention relates to a retainer package for a plurality of sutures and, more particularly, relates to a retainer package having a plurality of panel members which define individual suture compartments for storing sutures.

2. Description of the Prior Art

Packaging of surgical needles and sutures requires that the needles be secured properly to prevent displacement, as well as being simply and quickly removable from their packages for use by the surgeon. Jarring or displacement of such sharp, needles will tend to dull their edges and reduce their effectiveness while increasing trauma to the patient during use.

Also it is desirable to package the needle/suture combinations in a manner where they are sufficiently separated for ready access to the user when they are needed. Moreover, the suture packages must be capable of receiving and holding sutures of various sizes while generally not affecting the quality, shape or strength of the suture in any way.

In general, a most significant objective in suture packaging is to store and maintain the relatively delicate ligatures in some form of spaced relation to each other so that access and removal of the suture may be readily available without adversely affecting the ligature or the needle as noted hereinabove. The present invention is directed to a suture package wherein a plurality of sutures may be stored in a single package while maintaining the individuality of each suture with respect to the others.

SUMMARY OF THE INVENTION

The present invention provides a suture package comprising a card member, needle holding means associated with the card member for retaining at least two suture needles in respective fixed positions thereon and a plurality of suture panel members foldably connected to each other and arranged to fold upon each other to form a suture retainer having at least two individual suture compartments defined between pairs of adjacent panel members.

The card member comprises at least two card portions dimensioned and arranged to receive and enclose the suture retainer formed by the folded suture panel members. In a preferred embodiment, the card member comprises three card portions including a centrally positioned card portion comprising the needle holding means and first and second adjacent card portions foldably connected to the centrally positioned card portion along respective transverse edges thereof.

A suture compartment retaining flap is foldably connected to the centrally positioned card portion along a longitudinal edge thereof. The retaining flap is adapted to fold onto the folded suture panel members which are positioned on the centrally positioned card portion during packaging to retain the folded suture panel members against the centrally positioned card portion.

A needle protecting flap is connected to the first adjacent card portion along a longitudinal edge thereof. The needle protecting flap is adapted to fold along its longitudinal edge to enclose the butt ends of the secured suture needles. In a preferred embodiment, the needle protecting flap has a score line disposed along the mid-portion thereof, which defines first and second flap portions. The second flap portion is adapted to fold onto the first flap portion to enclose the butt ends of the secured suture needles. The second flap portion of the needle protecting flap also includes a projecting tab which extends beyond an upper edge defined by the card member when the card member is in a fully closed position.

A preferred needle holding means of the suture package comprises a plurality of tab portions and apertures formed in the card member, whereby respective pluralities of the tab portions are dimensioned and positioned to engage respective portions of the suture needles and corresponding apertures are adapted to receive the respective pointed ends of the suture needles. The tab portions may be respectively positioned in the card member to retain curved suture needles. Preferably, at least two of the tab portions are provided in the card member to retain each curved suture needle and one aperture is provided to receive the pointed end of each curved suture needle.

In an alternative preferred embodiment, the suture package comprises a card member, needle holding means associated with the card member for retaining at least two curved suture needles and a plurality of suture panel members. The suture panel members include a first row of at least three panels foldably connected to each other by fold lines along respective longer sides thereof, a second row of at least two panels foldably connected to each other by a fold line along respective longer sides thereof and a third row of at least one panel. The panels of the first, second and third rows are respectively foldable in a manner to form compartments between adjacent panels. Each compartment is adapted to contain at least one flexible suture portion therein in a coiled or figure eight configuration. The panels are preferably finally foldable to form a suture retainer. The card member of this alternative embodiment includes at least two card portions adapted to fold onto each other to define a retainer holding compartment to accommodate the suture retainer formed by the folded suture panels.

In another alternative preferred embodiment, the suture package comprises an enclosure card comprising a central panel member, a cover panel member foldably connected to the central panel member along a first transverse edge thereof, a locking panel member foldably connected to the central panel member along a second transverse edge thereof, means associated with the central panel member for retaining at least two suture needles and a plurality of suture panel members foldably connected to each other and arranged to fold upon each other to form at least two individual suture compartments between pairs of adjacent panel members. Each compartment is dimensioned to contain at least one flexible suture portion therein in a wound configuration. The folded suture panel members are positioned on the central panel member and enclosed within the enclosure card by respective folding of the cover panel member onto the folded suture panels and the locking panel member onto the cover panel member.

The needle holding means comprises a plurality of arcuate shaped tabs and corresponding apertures formed in the central panel member, respective plurality of the arcuate shaped tabs dimensioned and positioned to engage respective portions of the suture needles and respective corresponding apertures positioned to receive respective pointed ends of the suture needles. Preferably, the needle holding means comprises sufficient arcuate shaped tabs and apertures to retain at least five curved suture needles.

The locking panel member may include an arcuate locking tab configured and dimensioned to be received within a corresponding slot formed in the cover panel member to retain the enclosure card in a closed position about the folded suture panel members.

The present invention is also directed to a method of loading a suture retainer package with a plurality of sutures, each suture having a needle attached to at least one end thereof. The method comprises the steps of coiling a first suture on a first panel member of a plurality of panel members which are foldably connected to each other and arranged to fold upon each other to form a plurality of suture compartments, folding an adjacent panel member of the plurality of suture panel members onto the first panel member to form a first individual suture compartment between the first and adjacent panel members, repeating the aforementioned steps as desired to load a plurality of sutures and form a plurality of suture compartments to individually retain the sutures, securing the needles attached to the sutures to needle holding means of a card member having at least two card portions and positioning the folded suture panel members onto the card member and folding the two card portions onto each other to form a compartment to enclose the folded suture panel members.

The present invention is particularly useful for packaging gut sutures. However, other absorbable and nonabsorbable sutures can also be loaded and retained as described herein.

BRIEF DESCRIPTION OF THE DRAWINGS

Preferred embodiments of the invention are described hereinbelow with reference to the drawings wherein:

FIGS. 4–7 are perspective views of the blank sheet of FIG. 2 illustrating the preferred sequence of loading and folding the panel members to form individual suture compartments for five needled sutures;

FIG. 8 is a perspective view of a suture with attached needle wound in a figure eight configuration for storage in the individual suture compartments;

FIG. 9 is a frontal plan view of the package for multiple sutures illustrating the folded panel members secured within the enclosure card; and FIG. 10 is a frontal plan view of an outer envelope constructed to receive the retainer package of FIG. 1, with the retainer package shown in phantom within the envelope.

DESCRIPTION OF THE PREFERRED EMBODIMENTS

Figure 1:
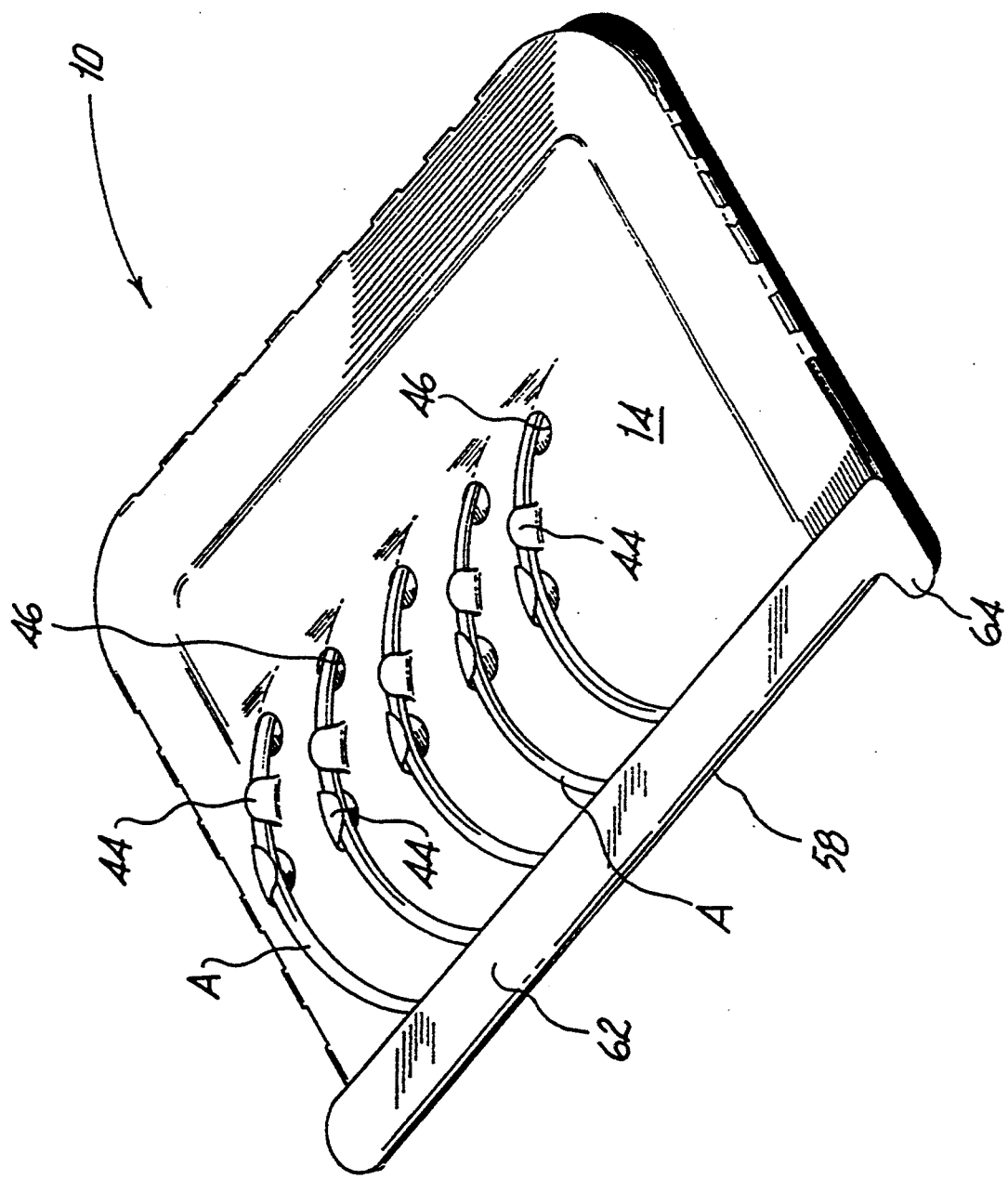
FIG. 1 is a perspective view of a retainer package for multiple sutures constructed according to the present invention.
Figure 2:
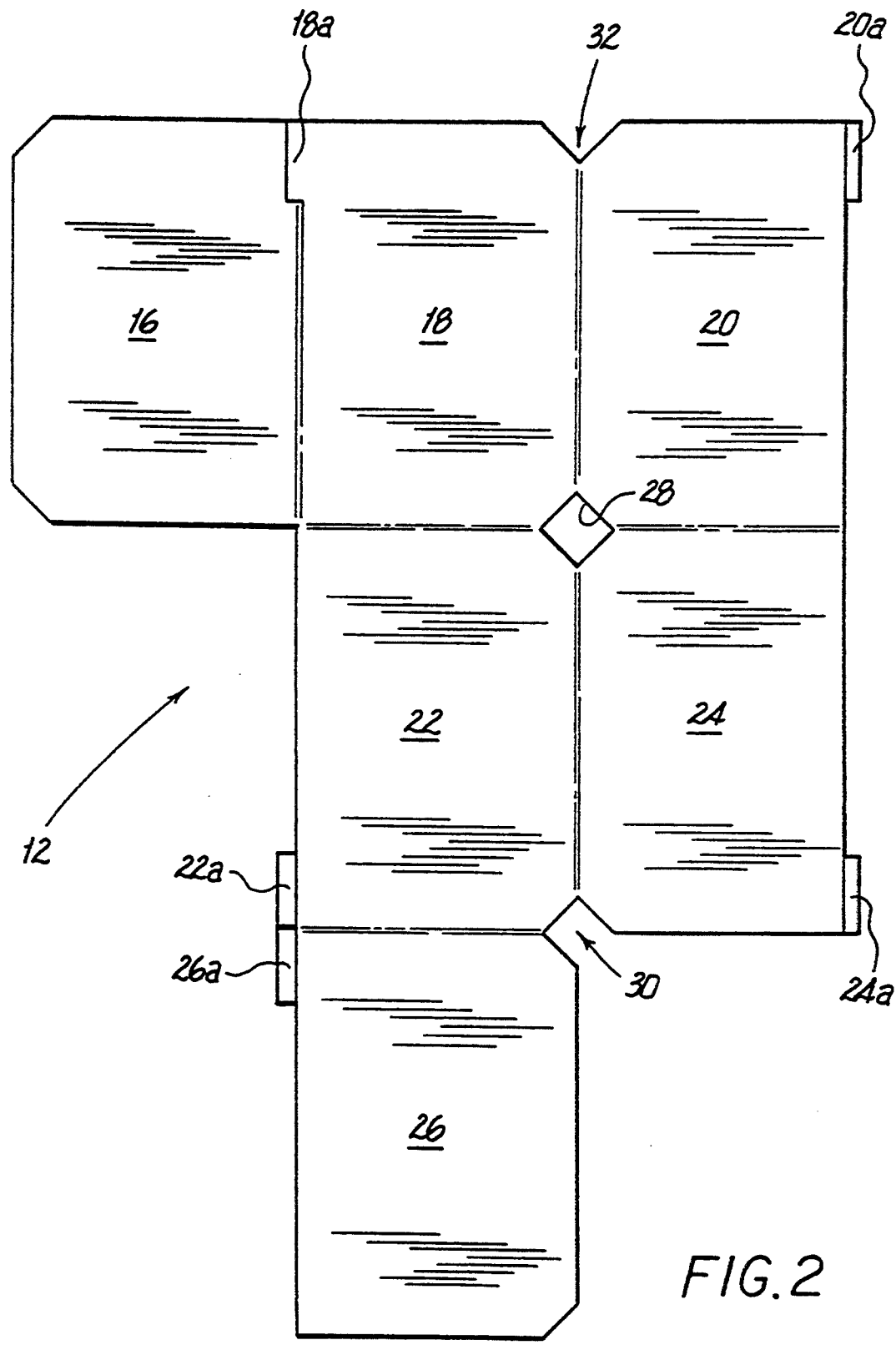
FIG. 2 is a plan view of a blank sheet constructed according to the invention defining a plurality of panel members foldably connected to each other.
Figure 3:
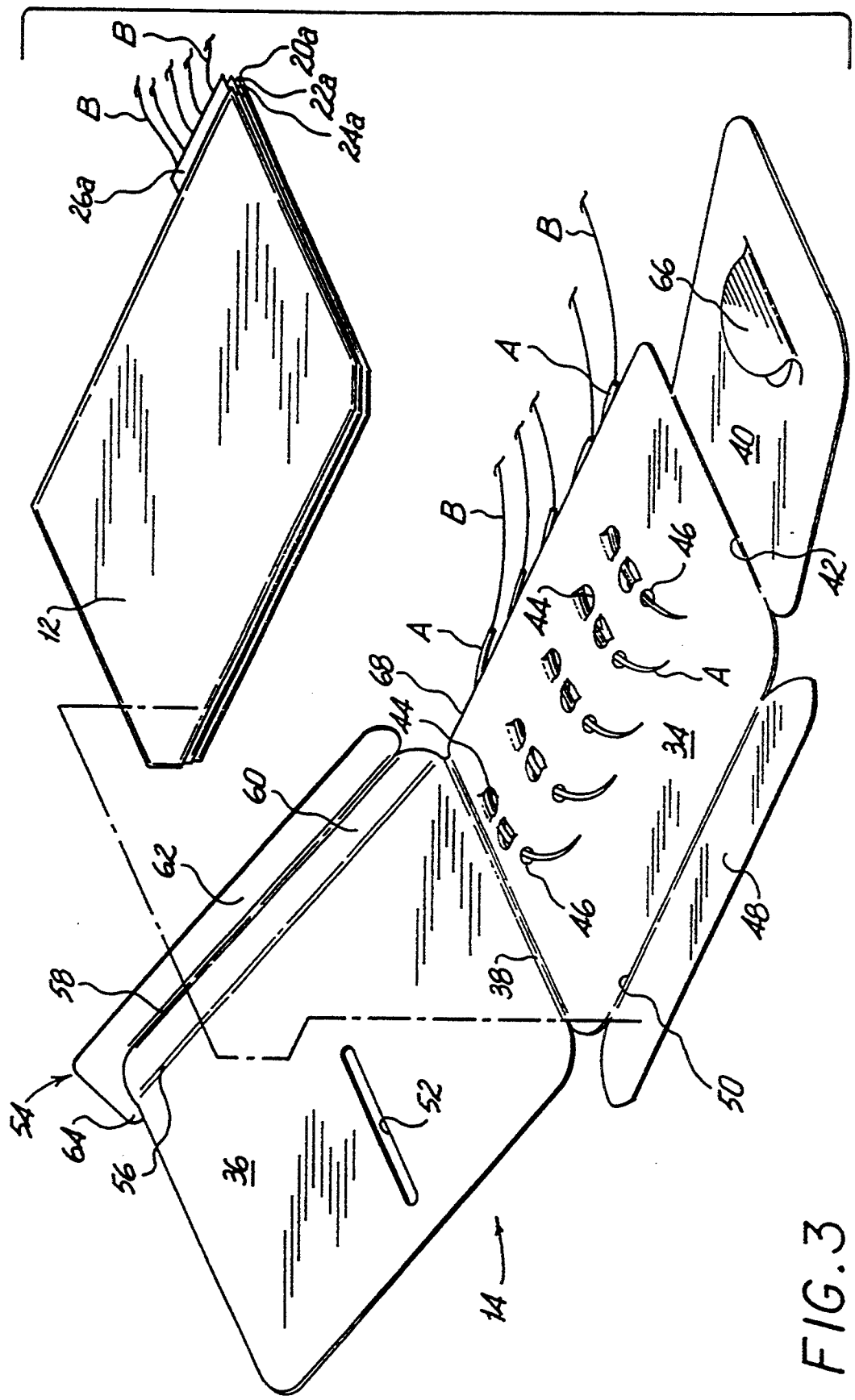
FIG. 3 is a perspective view illustrating the enclosure card in an unfolded condition with five needles secured in position prior to placement of the folded blank sheet within the card.

Referring to FIGS. 1–3, the retainer package 10 constructed according to the present invention is illustrated. FIG. 1 illustrates the package 10 in a completely folded and assembled condition. FIG. 2 is a plan view of a blank sheet 12 constructed according to the invention and defining a plurality of panel members foldably connected to each other to form individual suture compartments. FIG. 3 is a perspective view of an enclosure card 14 of the present invention and the blank sheet 12 of FIG. 2 fully folded. When the folded blank sheet 12 is positioned within the enclosure card and the enclosure card secured about the sheet, the suture package will appear as shown in FIG. 1.

Referring once again to FIG. 2, the blank sheet 12 is illustrated and includes separate and individual generally rectangular panels connected to each other as shown. Three rows of panels are provided. The first row includes three panel members 16, 18, 20 while the second row contains two panel members 22, 24. The third row contains one panel member 26. Panels 18, 20, 22, 24 and 26 include projecting flaps 18a, 20a, 22a, 24a, and 26a, respectively. A diamond shaped opening 28 is formed between the first and second rows of panels and a partial diamond shaped opening 32 is provided between the second and third rows of panels. An additional partial diamond shaped opening 32 is disposed adjacent panels 18 and 20. Openings 28, 30 and 32 receive upstanding winding pins of a wrapping fixture (not shown). Sheet 12 is preferably positioned on a winding fixture to facilitate loading of the panel compartments with the sutures.

Sheet 12 may be fabricated from paperboard, fiberboard or any other fibrous material such as Tyvek (a registered trademark of DuPont), which is a fibrous material constructed of spun bonded polyolefin fibers which are pressed together to form a sheet of fibrous material. Sheet 12 is preferably die cut to form the series of interconnected panels.

Referring now to FIG. 3, a perspective view of the enclosure card 14 of the present invention is illustrated. Enclosure card 14 is preferably formed from a single sheet of suitable material, e.g., stiff paper or paperboard such as 5 point to 12 point solid, Tyvek, bleached sulfate board, plastics, foils, laminates and the like which is die cut to provide the desired configuration.

Enclosure card 14 includes needle retaining panel 34, cover panel 36 foldably connected to one side of the retaining panel by a single fold line 38, and locking panel 40 foldably connected along the opposed side of the retaining panel by single fold line 42.

As best illustrated by FIG. 3 taken in conjunction with FIG. 1, retaining panel 34 includes five series of needle holding tabs 44 and needle point receiving apertures 46. Particularly, each series includes two holding tabs 44, with each tab alternately facing the next adjacent tab. Tabs 44 are adapted to be lifted from retaining panel 34 to engage the midportion of each needle A to retain the needles as shown in FIG. 1. The points of each needles A are positioned within apertures 46 and, accordingly, are retained within the interior of the package 10 when the package is in the closed position, thereby protecting the points of the needles.

Referring again to FIG. 3, a flap 48 is connected to a longitudinal side of retaining panel 34 along single fold line 50. Flap 48 is arranged to fold onto the folded suture compartments after the compartments are positioned on retaining panel 34. Flap 48 serves in retaining the folded suture panels against retaining panel 34 and also in enclosing the sutures B loaded within each compartment to prevent release of the sutures through the sides of the folded compartments.

Cover panel 36 is adapted to fold along score line 38 onto folded sheet 12. Cover panel 36 includes slot 52 which is provided to secure the enclosure card 10 about folded sheet 12 as will be described. A needle protecting flap 54 is connected to a longitudinal side of cover panel 36 along single score line 56. A longitudinal perforated score line 58 extends along the midline of protecting flap 54. Score line 58 defines first and second flap portions 60, 62, respectively. Second flap portion 62 is arranged to fold onto first flap portion 60 to enclose the butt ends of the needles A, which ends extend beyond the side of retaining panel 34 as shown in FIG. 3 when secured to the retaining panel. Second flap portion 62 also encloses the sutures loaded within folded sheet 12. FIG. 1 illustrates protecting flap 54 in a folded condition enclosing the secured suture needles.

Referring again to FIG. 1 in conjunction with FIG. 3 a projecting tab 64 extends outwardly from second flap portion 62. Tab 64 is advantageously dimensioned and positioned to be grasped by the surgeon during opening of the package 10 such that second flap portion 62 is readily detached along score line 58 from first flap portion 60 to expose the butt ends of the secured needles to facilitate needle removal.

Referring again to FIG. 3, locking panel 40 is arranged to fold onto folded cover panel 36 and possesses arcuate-shaped tab 66 which engages corresponding slot 52 formed in the cover panel to secure enclosure card 14 about the folded sheet 12. FIG. 9 illustrates the interlocking arrangement of tab 66 and slot 52 in detail.

Retainer 10 is suitable for storing both absorbable sutures and nonabsorbable sutures, e.g. catgut, silk, nylon, polyester, polypropylene, linen, cotton and absorbable synthetic materials such as polymers and copolymers of glycolic and lactic acids.

Figure 6:
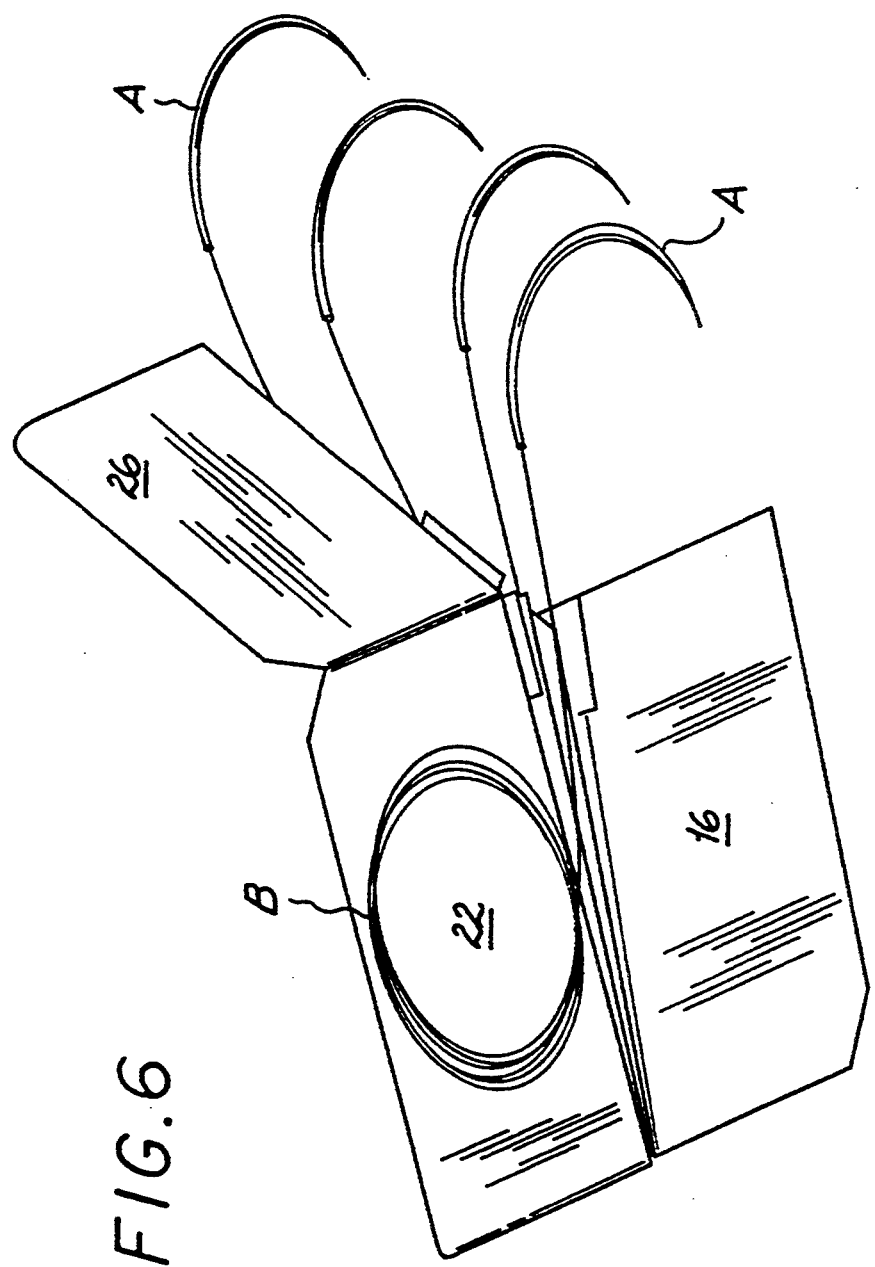

Referring now to FIGS. 4–7, the preferred procedure for loading five individual sutures B with attached needles A within sheet 12 is illustrated. Referring initially to FIG. 4, sheet 12 is shown in the fully unfolded condition. As previously mentioned, sheet 12 may be positioned on a suture winding fixture in the aforedescribed manner to facilitate the packaging operation. Individual sutures B are wound on panel 18 of the first row of panels and panel 22 of the second row. Thereafter, adjacent panels 20, 24 are folded onto the loaded sutures to form first and second individual compartments between the adjacent panels. Referring now to FIG. 5, a third suture B is wound on the rear side of panel 20. Thereafter, the lower portion of the sheet 12 including panels 22, 24 and 26 are folded onto the coiled suture to form a third suture compartment between panels 20 and 24 as shown in FIG. 6.

Figure 7:
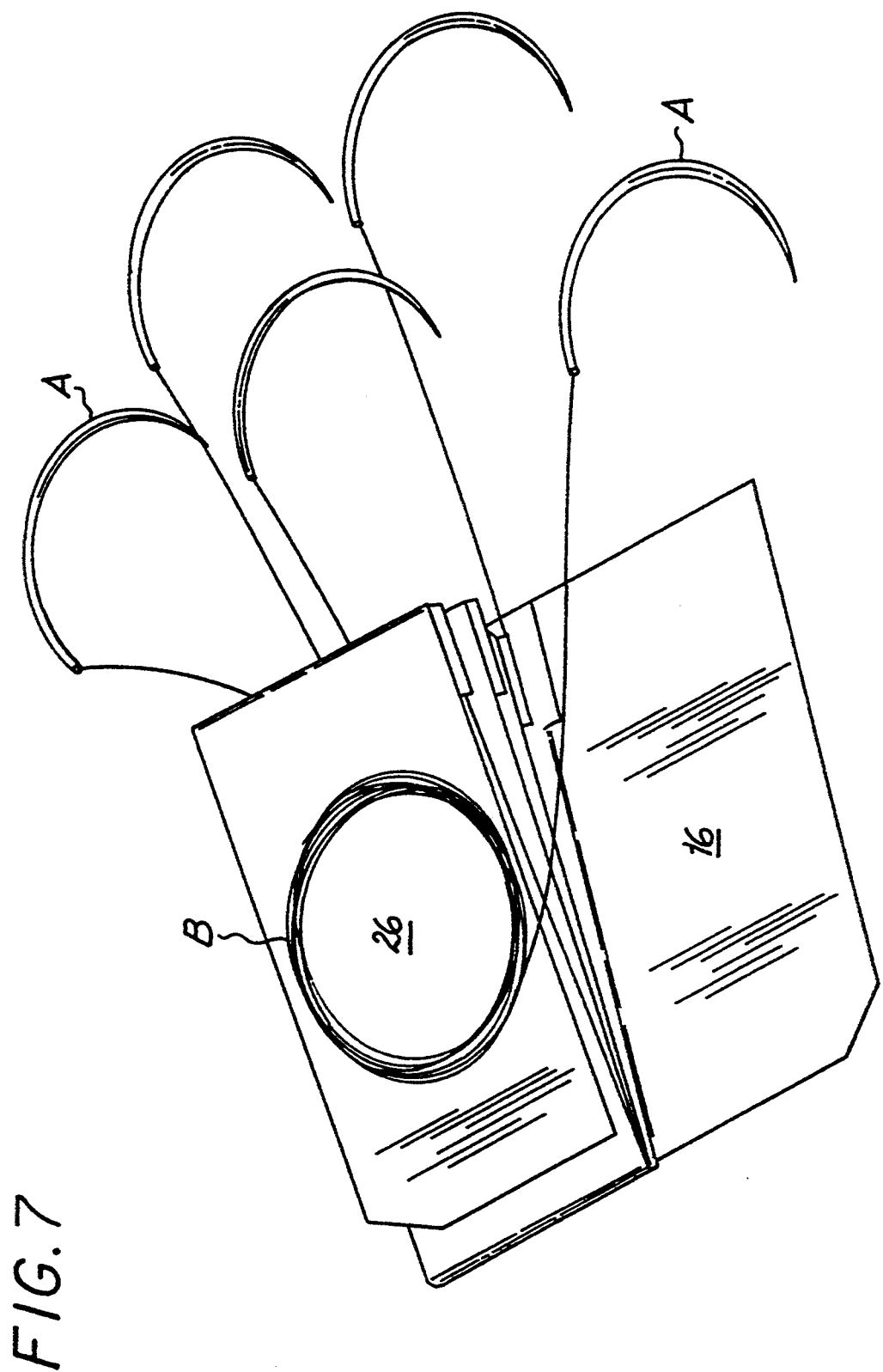

The packaging of the sutures is continued by coiling a fourth suture B onto the rear side of panel 22 and folding panel 26 onto the fourth suture B to form a fourth suture compartment. Referring now to FIG. 7, a fifth suture B is positioned on the rear side of panel 26 and remaining panel 16 is folded onto the suture to form the completely folded sheet shown in FIG. 3.

Although, the preferred procedure for loading the sutures within the individual suture compartments incorporates winding the sutures B such that each suture assumes a spiral or coiled configuration, it is to be appreciated that the sutures B may be wound in a figure-eight configuration as shown in FIG. 8 and positioned within the suture compartments as well. In addition, an alternative method of loading sutures into the retainer of the present invention incorporates a rolling fixture device which serves to insert individual sutures into the retainer subsequent to folding. Sutures loaded in this manner generally assume a figure eight configuration. After loading, a panel similar to 48 in FIG. 3 is folded to prevent release of the sutures through the sides of the folded compartments.

Referring again to FIG. 3, once sheet 12 is fully folded and loaded with sutures B, the individual suture needles A are positioned beneath the needle holding tabs 44 to retain the needles in position with the points of the needles inserted within their respective openings 46. The needles A are secured in a manner so that the butt ends partially extend beyond longitudinal side 68 of retaining panel 34. Such positioning presents the butt ends of the needles to the surgeon upon opening of the package so as to facilitate removal of the needles and attached sutures from their compartments. The respective suture end portions extending from the folded compartments are segregated from each other by projecting tabs 18a, 20a, 22a, 24a and 26a, thus minimizing the potential for entanglement of the adjacent suture portions.

Once all of the suture needles are secured, the folded sheet 12 is positioned on retaining panel 34. Side panel 48 is folded along score line 50 onto the folded sheet 12 to retain the sheet against retaining panel 34. Cover panel 36 is then folded onto folded sheet 12. Second flap portion 62 of needle protecting flap 54 is folded along perforated score line 58 to enclose the butt ends of needles A. Thereafter, locking panel 40 is folded onto cover panel 36 and locking tab 66 is inserted within corresponding slit 52 in cover panel 36 to secure enclosure card 14 about folded sheet 12 to form the fully closed suture package 10 illustrated in FIG. 9.

Preferably, the entire secured package 10 is packaged in a foil envelope 70 of the type shown in FIG. 10, which includes two sheets of foil sealed together along their respective peripheries to form a pocket to receive the suture package 10. An alcohol conditioning fluid may be added to envelope 70 to preserve the integrity of the gut suture material.

Upon opening the foil envelope 70 with suture package 10 loaded therewithin, the surgeon tears along tear line 72 to expose the package 10. Preferably, the tear line 72 is appropriately positioned so that projecting tab 64 of needle protection flap 54 is engaged by the surgeon as outer envelope 70 is opened, thereby causing second flap portion 62 of needle protecting flap 54 to be detached from first flap portion 60 along perforated score line 58 to expose the butt ends of the needles A. In the alternative, engagement of projecting tab 64 may cause the entire needle protecting flap 54 to be detached from cover panel 36. In either situation, the needles with attached sutures may be thereafter withdrawn from the package 10 by grasping the respective butt ends of the needles A with a grasping instrument or the like while the sheet 12 remains in the folded condition.

Although the present invention has been shown and described in terms of a preferred embodiment, it will be appreciated that various changes and other modifications are contemplated within the spirit and scope of the present invention as defined by the following claims.

What is claimed is:

1. A suture retainer package which comprises:
   a) a plurality of suture panel members foldably connected to each other and arranged to fold upon each other to form at least two individual suture compartments between pairs of adjacent panel members; and b) an individual card member dimensioned and arranged to receive and at least partially enclose said folded suture panel members, said card member including at least two card portions foldably connected to each other, one of said at least two card portions including a plurality of needle retaining tab portions formed therein, wherein respective pluralities of said tab portions are dimensioned and positioned to engage respective portions of at least two suture needles to retain the two suture needles in respective fixed positions thereon.

2. The package according to claim 1, wherein said card member comprises three said card portions, a centrally positioned card portion comprising said needle retaining tab portions and first and second adjacent card portions foldably connected to said centrally positioned card portion along respective transverse edges thereof.

3. The package according to claim 2 wherein said folded suture panel members are positioned on said centrally positioned card portion.

4. The package according to claim 3 wherein a suture compartment retaining flap is foldably connected to said centrally positioned card portion along a longitudinal edge thereof, said retaining flap adapted to fold onto said folded suture panel members positioned on said centrally positioned card portion to retain said folded suture panel members against said centrally positioned card portion.

5. The package according to claim 4 wherein a needle protecting flap is connected to said first adjacent card portion along a longitudinal edge thereof, wherein when said first adjacent card portion is folded onto said folded suture panel members positioned on said centrally positioned card portion said needle protecting flap is folded along said longitudinal edge to enclose the butt ends of said secured suture needles.

6. The package according to claim 5 wherein said needle protecting flap has a score line disposed along the midportion thereof, said score line defining first and second flap portions, said second flap portion adapted to fold onto said first flap portion to enclose the butt ends of said secured suture needles.

7. The package according to claim 6 wherein said second flap portion of said needle protecting flap comprises a projecting tab which extends beyond an upper edge defined by said card member when said card member is in a fully closed position.

8. The package according to claim 3 wherein said second adjacent card portion comprises an arcuate tab configured and dimensioned to engage a corresponding slit formed in said first adjacent card portion to secure said card member in a fully closed position about said folded suture panels.

9. The package according to claim 1 wherein said tab portions formed in said card member are respectively positioned to retain curved suture needles.

10. The package according to claim 12 wherein at least two of said tab portions are provided in said card member to retain each curved suture needle and one said aperture is provided to receive the pointed end of each curved suture needle.

11. The package according to claim 10 wherein said needle holding means comprises sufficient tab portions and corresponding apertures to retain at least five curved needles.

12. The package according to claim 1 wherein at least three rows of said suture panel members are foldably connected to each other.

13. The package according to claim 12 wherein said suture panel members of a first row are foldably connected to each other along longitudinal sides thereof.

14. The package according to claim 13 wherein said suture panel members of a second row are foldably connected to each other along longitudinal sides thereof.

15. The package according to claim 14 wherein said first and second rows of said suture panel members are connected to each other on the shorter sides of two suture panel members in each row.

16. The package according to claim 15 wherein said second row and a third row of said suture panel members are connected to each other on the shorter sides of one suture panel member in each row.

17. The package according to claim 16 wherein said first row comprises three said suture panel members.

18. The package according to claim 17 wherein said second row comprises two said suture panel members.

19. The package according to claim 18 wherein said third row comprises one said suture panel member.

20. A suture package which comprises:
a) an individual member;
b) a plurality of suture panel members, including:
   a first row of at least three panels foldably connected to each other by fold lines along respective longer sides thereof;
   a second row of at least two panels foldably connected to each other by a fold line along respective longer sides thereof, said first and second rows of panels being connected to each ther on the shorter sides of at least two suture panels in each row; and
   a third row of at least one panel, said second and third rows f panels being connected to each other on the shorter sides of at least one suture panel in each row;
c) needle holding means associated with said card member for retaining at least two suture needles; and
d) said panels of said first, second and third rows being respectively foldable in a manner to form compartments between adjacent panels, each compartment adapted to contain at least one suture portion therein, each suture portion attached to a needle held by said needle holding means of said card member, said panels being finally foldable to form a suture retainer.

21. The suture retainer package according to claim 20 wherein said card member includes at least two card portions, said at least two card portions adapted to fold onto each other to define a retainer holding compartment to accommodate said suture retainer formed by said folded suture panels.

22. The suture package according to claim 21 wherein said suture panel members are generally rectangular in shape.

23. A suture package, which comprises:
a) an individual enclosure card including a central panel member, a cover panel member foldably connected to said central panel member along a first transverse edge thereof, a locking panel member foldably connected to said central panel member along a second transverse edge thereof, said central panel member having at least two series of arcuate-shaped tab portions and apertures formed therein for retaining at least two suture needles, each series including a plurality of said tab portions and one said aperture, wherein said tab portions of each said series are dimensioned and positioned to engage respective portions of a curved surgical needle and wherein said corresponding aperture of said series is dimensioned to receive the respective pointed end of the suture needle;

b) a plurality of suture panel members foldably connected to each other and arranged to fold upon each other to form at least two individual suture compartments between pairs of adjacent panel members, each compartment adapted to contain at least one suture portion therein in a wound configuration, each suture attached to a needle held by said needle holding means; and c) said folded suture panel members being positioned on said central panel member and enclosed within said enclosure card by respective folding of said cover panel member onto said folded suture panels and said locking panel member onto said cover panel member.

24. The suture package according to claim 1 further including an individual suture portion stored within each said individual suture compartment, each said individual suture portion having at least one surgical needle attached thereto.

25. The suture package according to claim 23 wherein said central panel member comprises sufficient arcuate shaped tabs and apertures to retain at least three curved suture needles.

26. The suture package according to claim 25 wherein each said curved suture needle is retained by at least two of said arcuate tabs.

27. The suture package according to claim 23 wherein said locking panel member comprises an arcuate locking tab configured and dimensioned to be received within a corresponding slot formed in said cover panel member to retain said enclosure card in a closed position about said folded suture panel members.

28. The suture package according to claim 23 wherein at least two of said suture panel members have projecting tab members extending from respective longitudinal edges thereof, said tab members being dimensioned and configured to separate and prevent entanglement of the suture portions which extend from said folded individual suture compartments to said needle holding means of said central panel member.

29. The suture package according to clam 24 wherein each said individual suture portion is stored in an individual suture compartment in a coiled configuration.

30. The suture package according to claim 24 wherein each said individual suture portion is stored in an individual suture compartment in a figure eight configuration.

31. The suture package according to claim 24 wherein each said individual suture portions comprises an absorbable material selected from the group consisting of catgut and synthetic materials including polymers and copolymers of glycolic and lactic acids.

32. The suture package according to claim 24 wherein each said individual suture portions comprises a nonabsorbable material selected from the group consisting of silk, nylon, polyester, polypropylene, linen and cotton.

33. A suture retainer package comprising at least three rows of suture panel members foldably connected to each other and arranged to fold upon each other to form a plurality of individual suture compartments between pairs of adjacent panel members, each panel of each row having two longitudinal sides and two transverse sides and being foldably connected to an adjacent panel in the row along the longitudinal sides thereof, a first row of panels being connected to a second row of panels along the transverse sides of at least two panels in each said first and second rows, said second row being connected to a third row of panels along the transverse sides of at least one panel in each said second and third rows, wherein the first row has at least three panel members, the second row has at least two panel members and the third row has at least one panel member.

34. The suture package according to claim 13 further including an outer envelope dimensioned to accommodate said enclosure card in a closed condition having said suture panel members therein, said outer envelope having a tear line positioned in an upper portion thereof along which said outer envelope is opened, wherein said projecting tab of said enclosure card is at least partially disposed along said tear line of said outer envelope such that opening of said outer envelope along said tear line causes at least partial engagement with said projecting tab.

* * * * *